United States Patent [19]

Pisharodi

[11] Patent Number: 5,171,278
[45] Date of Patent: Dec. 15, 1992

[54] MIDDLE EXPANDABLE INTERVERTEBRAL DISK IMPLANTS

[76] Inventor: Madhavan Pisharodi, 500 Acacia Lake Dr., Brownsville, Tex. 78521

[21] Appl. No.: 659,758

[22] Filed: Feb. 22, 1991

[51] Int. Cl.$^5$ .............................................. A61F 2/44
[52] U.S. Cl. ........................................ 623/17; 606/61
[58] Field of Search ............... 623/17, 16, 18; 606/60, 606/61, 63; 128/69

[56] References Cited

U.S. PATENT DOCUMENTS

| | | | |
|---|---|---|---|
| 3,648,294 | 3/1972 | Shahrastani | 623/18 X |
| 3,867,728 | 2/1975 | Stubstad et al. | 623/17 |
| 4,309,777 | 1/1982 | Patil | 623/17 |
| 4,401,112 | 8/1983 | Rezaian | 606/61 |
| 4,553,273 | 11/1985 | Wu | 606/61 X |
| 4,834,757 | 5/1989 | Brantigan | 623/17 |
| 4,657,550 | 4/1987 | Daher | 606/61 X |
| 4,759,769 | 7/1988 | Hedman et al. | 623/17 |
| 4,772,287 | 9/1988 | Ray et al. | 128/69 X |
| 4,863,476 | 9/1989 | Shepperd | 623/17 |
| 4,863,477 | 9/1989 | Monson | 623/17 |
| 4,932,969 | 6/1990 | Frey | 623/17 |
| 4,932,975 | 6/1990 | Main et al. | 606/61 X |
| 5,059,193 | 10/1991 | Kuslich | 606/61 |

FOREIGN PATENT DOCUMENTS

| | | | |
|---|---|---|---|
| 2701279 | 7/1977 | Fed. Rep. of Germany | 606/63 |
| 3729600 | 3/1989 | Fed. Rep. of Germany | 623/17 |
| 2639823 | 6/1990 | France | 623/17 |
| 0662082 | 5/1979 | U.S.S.R. | 606/63 |
| 0906548 | 2/1982 | U.S.S.R. | 606/63 |
| 1122304 | 11/1984 | U.S.S.R. | 606/63 |

Primary Examiner—Randall L. Green
Assistant Examiner—D. Willse
Attorney, Agent, or Firm—Vaden, Eickenroht, Thompson, Boulware & Feather

[57] ABSTRACT

Artificial disk implant and methods for implanting it, the implant having a member for adapting in size and shape to an anatomical space between vertebrae and apparatus for expanding the member to conform to the space.

8 Claims, 1 Drawing Sheet

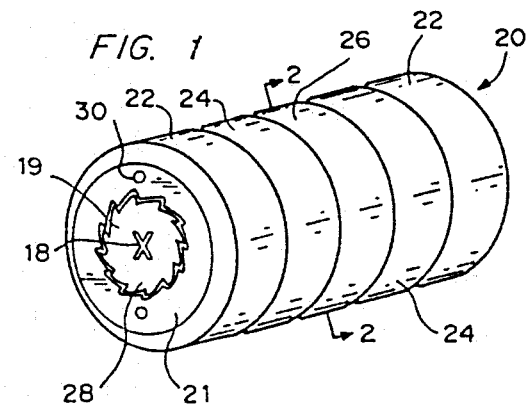
FIG. 1
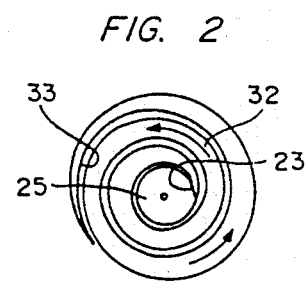
FIG. 2
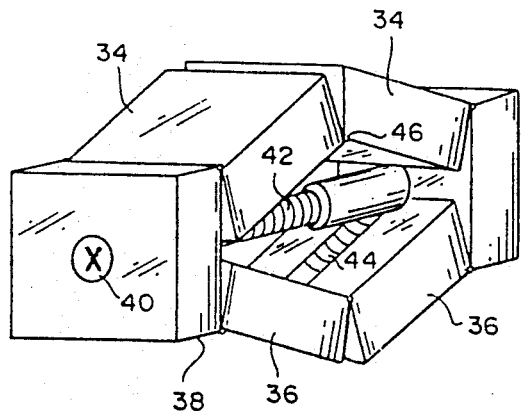
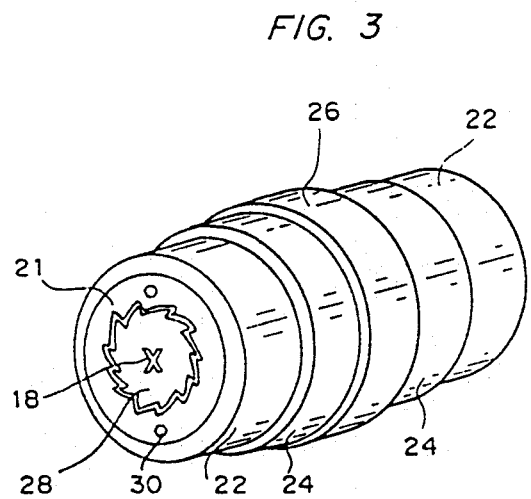
FIG. 3
FIG. 5
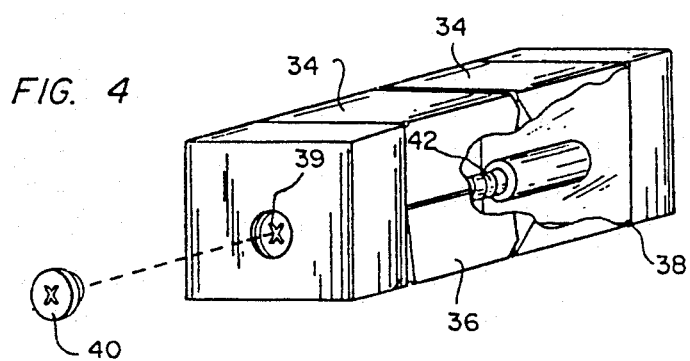
FIG. 4

MIDDLE EXPANDABLE INTERVERTEBRAL DISK IMPLANTS

RELATED APPLICATION

Filed on even date herewith is Applicant's application entitled Artificial Spinal Prosthesis, a copy of which is submitted herewith

BACKGROUND OF THE INVENTION

1. Field of the Invention

This invention relates to an artificial intervertebral disk implant. More particularly, the present invention relates to cylindrical and rectangular disk implants which are expandable in the middle and can be used alone or in various combinations for the purpose of spinal fusion.

2. Description of the Related Art

The spine is a flexible structure comprised of thirty-three vertebrae. The vertebrae are separated and cushioned from each other by fiber cartilage in structures called intervertebral disks. If the spine is injured or becomes diseased, these disks are surgically removed. Such disk injuries can happen in the neck, in the thoracic region and in the lumbar region. The more frequent injuries are in the lower lumbar and in the lower cervical regions.

Treatment of herniated disk in the neck and in the lumbar region continues to be a challenging field of medicine. The classical treatment for a ruptured disk continues to be removal of the disk which is normally needed between the vertebrae. In the process, a defect is made which continues to bother the patients throughout the rest of their life. One additional procedure previously attempted is to replace the disk space with a bone graft, thus, bringing about a spinal fusion, i.e. a fusion of the two vertebrae thus eliminating the empty space between the vertebrae.

Theoretically, this is a satisfactory procedure, though not ideal because the replaced bone does not have any of the functions of the cartilage tissue, i.e. no cushioning effect. This procedure, however, is technically demanding and has medical complications because of several physiological factors. First of all, the bone plug used to pack the disk space does not conform to the shape of the disk because the disk bulges maximally in the center. The disk space is wider in the middle and narrow at its anterior and posterior ends. It is impossible to insert a bone plug having its maximum width at the center because it cannot be inserted through the mouth of the disk space. For this reason, the various bone plugs have only four point contacts, i.e. at the front and back part of the disk space. Secondly, if the bone pieces do not fuse within a minimum period of time, they dissolve, become thinner and many eventually extrude out of the disk space, causing pressure on the nerve roots.

Various synthetic disk plugs have been proposed in the past, but all have the problem of not conforming to the shape of the disk space. There has long been a need for a disk plug capable of supporting the disk space after a simple diskectomy.

SUMMARY OF THE INVENTION

A synthetic intervertebral disk implant is described for implementation into the disk space after surgical removal of a diseased or damaged intervertebral disk. Implants according to this invention have a member for adapting to the anatomical region of the disk space and apparatus for expanding the member so it conforms to a portion of that space.

In one preferred embodiment, there is provided an artificial intervertebral disk implant having a cylindrical body comprised of cylindrical subunits capable of expansion. In another preferred embodiment, there is provided an artificial intervertebral disk implant having a rectangular body comprised of rectangular subunits capable of expansion. Both the cylindrical and rectangular implants are disk plugs expandable in the middle portion to provide contact with substantially the entire area of the disk space against the vertebral bodies.

The present invention recognizes and addresses the previously-mentioned long-felt needs and provides a satisfactory meeting of those needs in its various possible embodiments. To one of skill in this art who has the benefits of this invention's teachings and disclosures, other and further objects and advantages will be clear, as well as others inherent therein, from the following description of presently-preferred embodiments, given for the purpose of disclosure, when taken in conjunction with the accompanying drawings. Although these descriptions are detailed to insure adequacy and aid understanding, this is not intended to prejudice that purpose of a patent which is to claim an invention no matter how others may later disguise it by variations in form or additions of further improvements.

BRIEF DESCRIPTION OF THE DRAWINGS

So that the manner in which the above cited features, advantages, and objects of the invention as well as others which will become clear are attained and can be understood in detail. More particular description of the invention briefly summarized above may be had by reference to certain embodiments thereof which are illustrated in the appended drawings, which drawings form a part of the specifications. It is to be noted, however, that the appended drawings illustrate preferred embodiments of the invention and are therefore not to be considered limiting of its scope for the invention may admit to equally effective equivalent embodiments.

In the accompanying drawings FIG. 1 is a side elevation view of the cylindrical disk implant.

FIG. 2 is a side elevation view of an expanded cylindrical disk implant.

FIG. 3 is a cross section view of the implant.

FIG. 4 is a side elevation view of the rectangular disk implant.

FIG. 5 is a side elevation view of an expanded rectangular disk implant.

DETAILED DESCRIPTION OF THE INVENTION

The disk implants of the present invention can be understood with FIGS. 1 to 5 in which the numerals represent like parts. FIG. 1 depicts a cylindrical embodiment of the present invention. A disk implant 20 is comprised of a strong thin non-porous material. Suitable materials for the disk implant 20 include, modified carbon, titanium, steel, any surgical implant material or any biologically compatible material. The disk implant 20 is comprised of a plurality of subunits 22, 24 and 26 as screw 28 may be turned to cause expansion of subunits 24 and 26. The expanded shape of the disk implant 20 is shown in FIG. 2. Turning screw 28 allows for maximal expansion of the subunit 26 and moderate expansion of the subunit 24.

Turning of Phillips screw 28 expands subunits 24 and 26 which remain in an expanded shape due to the lock nut 21. Removal of lock nut 21 is accomplished by turning of the allen screw 30 which holds lock unit 21 to subunit 22.

Lock nut 21 is inlaid into end subunit 22 and is fixed by the allen screw. Lock nut 21 is removed if the implant has to be removed.

FIG. 2 illustrates a cross section of the disk implant 20. By adjusting the diameter of the screw shaft (not pictured) and thickness of the cylindrical sheets, the subunits 24 and 26 can be expanded as desired. The cylindrical disk implant 20 is expanded as the sheets 32 are uncoiled. Generally, any method that allows for expansion of either embodiment of the disk implant may be used. For the cylindrical disk implant, turning the screw uncoils the sheets because the inside end of the sheet is attached to the screw.

FIG. 3 illustrates the cylindrical disk implant in its expanded form. In its expanded form, the implant cannot be removed from the disk space.

FIG. 4 depicts a rectangular disk implant 31 according to the present invention. Turning Phillips head 39 of screw 42 encapsulated in a sheet 44 allows rotation of a hinge 38 of intermediate subunits 34 superiorly and rotation of inferior intermediate subunits 36 inferiorly. In the rectangular implant, subunits 32 are not mobile. The expanded shape of the rectangular disk plug 31 is illustrated in FIG. 5. Intermediate parts 34 and 36 are secured to an end part 32 by hinge 38. Intermediate parts 34 and 36 are secured to each other by hinge 46. Lock nut 40 is inserted over Phillips screw head 39. Lock nut 40 prevents the subunits from moving from the expanded shape. Removing lock nut 40 allows subunits 34 and 36 to uncoil.

The cylindrical and rectangular implants can be inserted after a simple diskectomy. Ordinarily, the size of the disk implant will be approximately 2.5 to 3.5 centimeters in length and 1.0 to 1.5 centimeters in height and width.

These disk implants are expandable in the middle portion so as to contact substantially the entire anterior-posterior length of the disk space against the vertebral bodies. If a complete intervertebral fusion is desired, this plug can be used in conjunction with intervertebral cancellous bone packing. Because of the support provided by the plug, in the initial stages until the fusion is established, the cancellous bone pieces have a better chance of fusion and also it has a better chance of staying in the intervertebral disk space. Alternately, the intervertebral disk plug can be used to maintain the disk height and this plug can be used in conjunction with intertransfers posterior lateral fusion. In short, this plug, which can be expanded in the middle, is going to act as a physiological support for the rest of the patient's life or until a bone fusion is established.

The disk implants of the present invention may have additional indications, e.g. short segment scoliosis where the curvature of the spine can be corrected by distracting the vertebral bodies on the inside of the curvature. By expanding the plugs inside the disk space the vertebral bodies are distracted and this can help straighten the spinal column.

If no bone graft is being planned it is recommended that the diskectomy be made minimally through one side exposures so that when the disk plug is inserted and expanded, it will take the empty room in the space. Because there is no further movement at this disk space, the chance of recurrent disk herniation will be minimized. Also the recurrent disk herniation is due to the opening and closing effect of the disk space towards the side where diskectomy is done and since the disk plug closed this mouth, the mouth cannot be opened and closed. By doing this process, in addition to one sided simple diskectomy, the risk of recurrent disk herniation can be reduced.

Two preferred types of disk plugs are proposed: one is rectangular and the other one is cylindrical. Both have the common feature of being expandable in the middle without changing the diameter of the dimensions of the two ends. The surgery is performed as in simple diskectomy and through a small laminotomy the disk is exposed. The disk material is removed and the nerve root compression is corrected. The posterior longitudinal ligament and disk cartilage are removed until the vertebral surfaces are exposed above and below the disk space. Depending upon the disk plug used, the disk space is fashioned either cylindrically or in a rectangular fashion. The disk plug is then inserted and hammered into place so that the anterior end of the disk plug will be almost touching the anterior longitudinal ligament. Subsequently, using a Phillips screw driver, the posterior screw end is turned. This also gives a good distraction to the vertebral bodies. In simple disk problems no further treatment is required.

When used alone without bone grafts, these disk implants should reduce the possibility of recurrent disk herniations. This is accomplished by a decrease in the mobility of the disk and the decrease in the disk mouth space.

If, however, an interbody fusion is desired, cancellous bone chips are made into very fine particles and pumped into the disk space medial to the disk plug and packed into the space. The posterior longitudinal ligament is intact to the opposite side and to the center of the disk space. These cancellous bone chips are held tightly in place. Since the mouth of the disk space is closed with the disk plug, the risk of the cancellous bone chips coming out is minimized. Also, the disk plug will prevent opening and closing of the disk space, thus preventing the bone chips coming out. If necessary, a small amount of glue can be applied over the cancellous bone chips just medial to the disk plug to close off the remaining portion of the opening of the disk space. The patient should be able to ambulate soon after the surgery because of the stability given by the disk plug. Before narrowing of the disk space occurs, the cancellous bone chips will have started the fusion process.

If on the other hand, the posterior lateral intertransverse fusion is desired, this procedure may be done in conjunction with the middle expandable disk plug. The disk plug is applied as explained above and then the surgeon does the posterior lateral fusion. Since the disk plug provides stability to the spine until the posterior lateral fusion is solid, the patient can ambulate soon after the surgery. Also this prevents the disk space narrowing which is a common problem with posterior lateral fusion.

The disk plugs can be made of any suitable material including a material like modified carbon so that they will be magnetic resonance imaging (mri) compatible. This is a simple and safe procedure with a wide range of applications in the management of low back pain. The same plug in smaller dimensions can be used in thoracic and cervical levels where indicated. In the neck this can be used following the anterior cervical diskectomy without the risk of the plug migrating anteriorly or posteriorly.

There is provided in preferred embodiments an artificial intervertebral disk implant having a cylindrical body comprised of cylindrical coils capable of expansion and intervertebral disk implant having a rectangular body comprised of rectangular blocks capable of expansion in the middle. Both the cylindrical and rectangular implants are disk plugs being expandable in the middle portion so as to provide contact with substantially the entire anterior posterior length of the disk space against the vertebral bodies.

The present invention recognizes and addresses the previously mentioned long felt needs and provides a satisfactory meeting of those needs in its various possible embodiments. To one of skilled in this art who has the benefits of this inventions teachings and disclosures other and further objects and advantages will be clear as well as others inherit their end from the following description of presently preferred embodiments given for the purpose of disclosure when taken in conjunction with the accompanying drawings. All those descriptions are detailed to insure an aid in understanding. This is not intended to prejudice the purpose of a patent which is to claim an invention no matter how others may later disguise it by variations in form or additions are further improvements.

I claim:

1. A method of implanting an intervertebral disk unit between two vertebrae after removal of a diseased or damaged intervertebral disk from therebetween, the disk unit being cylindrical in shape and comprising a member capable of adapting to the shape of an anatomical region of said disk space and means for variably expanding said member to substantially conform the shape of said member to the shape of a portion of said disk space, comprising the steps of:
   (a) inserting said disk unit into said disk space;
   (b) expanding the middle of said disk unit without changing the diameter of the dimensions of the ends thereof; and
   (c) introducing cancellous bone particles into said disk space and allowing said particles to fuse.

2. The method of claim 1, further comprising: contacting an adhesive substance medially to said disk unit to close off the disk space.

3. The method of claim 1, wherein said cancellous bone particles are introduced into said disk space medial to the disk unit.

4. A method of implanting an artificial intervertebral disk unit between two vertebrae after removal of a diseased or damaged intervertebral disk, the disk comprising a rectangular member comprised of a plurality of rectangular subunits including interconnected end and intermediate subunits, capable of adapting to an anatomical region of a disk space and means for variably moving the intermediate rectangular subunits so that said implant conforms to anatomical boundaries of the disk space, comprising the steps of:
   (a) inserting said disk unit into said disk space; and
   (b) expanding said disk unit, wherein said means for moving the intermediate subunits includes screw means threadedly received in the end subunits.

5. The method of claim 4, further comprising: tightening lock nut means against said screw means to prevent movement of said intermediate subunits.

6. A method of implanting an artificial intervertebral disk unit between two vertebrae after removal of a diseased or damaged intervertebral disk, the disk unit comprising a member capable of adapting to an anatomical region of a disk space and means for variably expanding said member to allow said member to substantially conform to a portion of said disk space, comprising the steps of:
   (a) inserting said disk unit into said disk space;
   (b) expanding said disk unit;
   (c) introducing cancellous bone particles into said disk space; and
   (d) contacting an adhesive substance medially to said disk unit to close off said disk space.

7. A method of implanting an intervertebral disk unit between two vertebrae after removal of a diseased or damaged intervertebral disk from therebetween, the disk unit being rectangular in shape and comprising intermediate and end subunits forming a member capable of adapting to the shape of an anatomical region of said disk space and means for variably expanding said member to substantially conform the shape of said member to the shape of a portion of said disk space, comprising the steps of:
   (a) inserting said disk unit into said disk space;
   (b) expanding the intermediate subunits comprising the middle of said disk unit without expanding the subunits comprising the ends thereof; and
   (c) introducing cancellous bone particles into said disk space and allowing said particles to fuse.

8. The method of claim 7, wherein said cancellous bone particles are introduced into said disk space medial to the disk unit.

* * * * *